United States Patent
Schelling et al.

(10) Patent No.: US 8,519,179 B2
(45) Date of Patent: Aug. 27, 2013

(54) METHOD OF MEASURING ENTRY OF WATER INTO PHOSGENE-CONDUCTING PLANTS

(75) Inventors: Heiner Schelling, Kirchheim (DE); Ulrich Penzel, Tettau (DE); Eckhard Stroefer, Mannheim (DE); Dirk Hablawetz, Frankenthal (DE); Dave Beckwith, Baton Rouge, LA (US); Kai Thiele, Antwerpen (DE); Johannes Jacobs, Ossendrecht (NL); Matthias Eiermann, Limburgerhof (DE); Uwe Storck, Ludwigshafen (DE); Jon S. Speier, Baton Rouge, LA (US); Thomas Grzanka, Baton Rouge, LA (US); William Portwood, Baton Rouge, LA (US)

(73) Assignee: BASF SE, Ludwigshafen (DE)

( * ) Notice: Subject to any disclaimer, the term of this patent is extended or adjusted under 35 U.S.C. 154(b) by 66 days.

(21) Appl. No.: 13/380,357

(22) PCT Filed: Jun. 23, 2010

(86) PCT No.: PCT/EP2010/058909
§ 371 (c)(1),
(2), (4) Date: Dec. 22, 2011

(87) PCT Pub. No.: WO2010/149701
PCT Pub. Date: Dec. 29, 2010

(65) Prior Publication Data
US 2012/0108844 A1    May 3, 2012

(30) Foreign Application Priority Data
Jun. 24, 2009    (EP) .................................... 09163666

(51) Int. Cl.
*C07C 263/00*    (2006.01)

(52) U.S. Cl.
USPC .......................................................... 560/347

(58) Field of Classification Search
None
See application file for complete search history.

(56) References Cited

U.S. PATENT DOCUMENTS

| 2010/0217035 | A1 | 8/2010 | Knoesche et al. |
| 2011/0124908 | A1 | 5/2011 | Rumpf et al. |
| 2011/0251425 | A1 | 10/2011 | Penzel et al. |
| 2011/0263892 | A1 | 10/2011 | Breuninger et al. |

FOREIGN PATENT DOCUMENTS

| DE | 28 09 322 | 9/1978 |
| DE | 139 955 | 1/1980 |
| DE | 100 27 779 | 12/2001 |
| JP | 8261914 | 10/1996 |
| JP | 2008 128783 | 6/2008 |
| WO | 2009 013303 | 1/2009 |
| WO | 2010 121997 | 10/2010 |

OTHER PUBLICATIONS

Abstract, DERWENT (DWPI) citation DD 139955 Jan. 30, 1980.*
U.S. Appl. No. 13/479,961, filed May, 24, 2012, Stroefer, et al.
International Search Report issued on Aug. 12, 2010 in PCT/EP10/08909 filed on Jun. 23, 2010.
U.S. Appl. No. 13/256,541, filed Sep. 14, 2011, Mattke, et al.
U.S. Appl. No. 13/266,049, filed Oct. 24, 2011, Stroefer, et al.

* cited by examiner

*Primary Examiner* — Karl J Puttlitz
(74) *Attorney, Agent, or Firm* — Oblon, Spivak, McClelland, Maier & Neustadt, L.L.P.

(57) ABSTRACT

The invention relates to a method of measuring entry of water and resulting corrosion in plants for producing isocyanates by reacting phosgene with one or more primary amines in a solvent. The invention further relates to an apparatus for producing such isocyanates, in the work-up section of which probes for monitoring corrosion are arranged in defined places.

Figure 1:
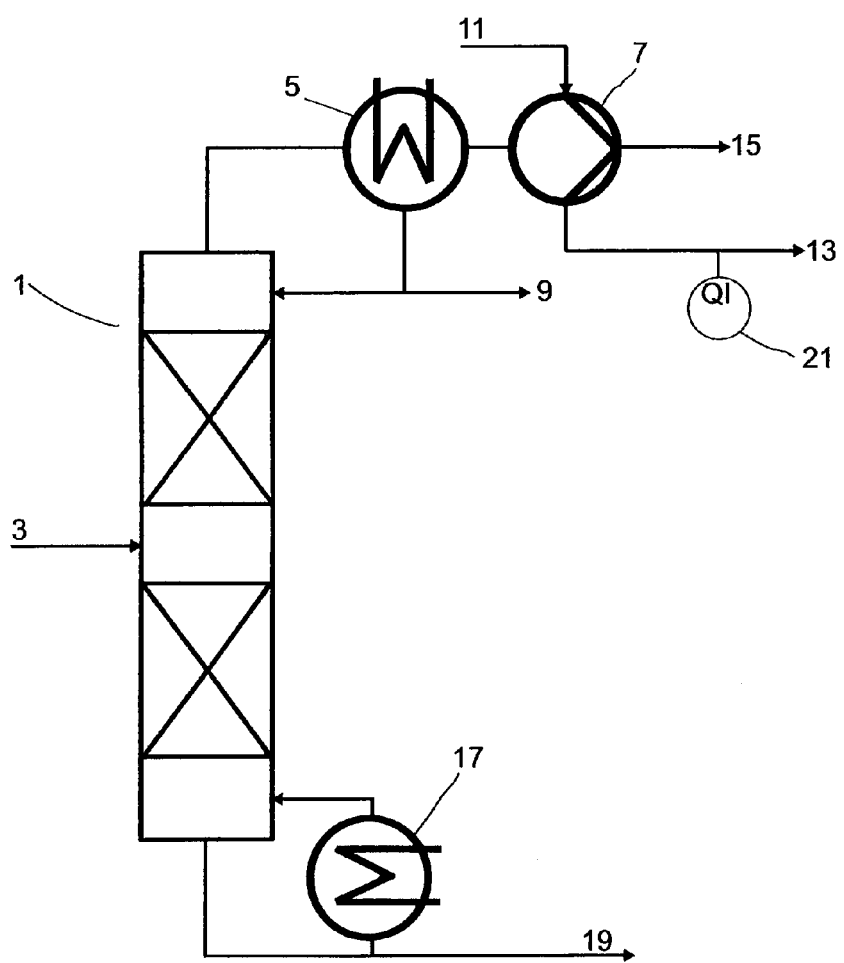

16 Claims, 2 Drawing Sheets ness of the plants, which is associated with high costs.
METHOD OF MEASURING ENTRY OF WATER INTO PHOSGENE-CONDUCTING PLANTS The invention relates to a method of measuring entry of water and resulting corrosion in plants for producing isocyanates by reacting phosgene with one or more primary amines in a solvent. The invention further relates to an apparatus for producing such isocyanates, in the work-up section of which probes for monitoring corrosion are arranged in defined places.

Isocyanates and isocyanate mixtures can be prepared by known processes by reacting primary amines or hydrochlorides thereof with an excess of phosgene. Here, the starting materials, viz. the primary amine and the phosgene, are usually fed together with a solvent into a mixing unit which is located upstream of a reactor. After mixing in the mixing unit, the mixture produced in this way is transferred into a reactor and reacted to form the corresponding isocyanate. After this reaction, the reaction mixture is passed to a work-up section of the plant which is located downstream of the reaction section and in which a work-up to give product streams comprising isocyanate, solvent and by-products is carried out. The worked-up solvent is usually fed back into the process.

Due to the presence of phosgene, both in the reaction section and in the work-up section of the above-described plants, there is a risk that in the event of entry of water phosgene will react with water to form $CO_2$ and hydrochloric acid which in the presence of further water can lead to corrosion damage. Such corrosion damage is difficult to predict but leads to long downtimes of the plants, which is associated with high costs.

A document which is concerned with the detection of the entry of water into phosgene or phosgene-conducting plants is DD-A 139 955. This document discloses the Installation of measuring facilities which can detect the occurrence of small traces of water at endangered places in the plant. Endangered places are defined, in particular, as heat exchangers which can have leaks due to environmental stress crack corrosion, welding pores or material defects.

Measurement probes for monitoring corrosion are known to those skilled in the art. DE-A 28 09 322 discloses, for example, probes for monitoring corrosion in a medium. Here, electrodes made of the material endangered by corrosion are introduced in a probe housing into the corrosive medium. The electrodes cause a continual current to flow, and the magnitude of this depends on the degree to which the electrodes are corroded. The electrodes are connected in a known manner to a resistance measuring bridge, with the electrodes of the probe forming a leg of a Wheatstone bridge. The other legs of the bridge are formed, inter alia, by a monitoring element and a reference element which are each not exposed to the corrosive medium but are isolated therefrom in another part of the probe housing.

It is an object of the present invention to provide a method of monitoring and measuring entry of water and thus of monitoring corrosion in plants for preparing isocyanates by reacting phosgene with one or more primary amine(s). A further object of the present invention is to provide an apparatus for preparing isocyanates which allows recognition of entry of water and the resulting occurrence of corrosion.

The object is achieved by a method of measuring entry of water into plants for preparing isocyanates by reacting phosgene with one or more primary amine(s) in a solvent, with these plants comprising a reaction section and a work-up section with solvent recovery. The method of the invention comprises the steps (a) introduction of at least one measurement probe into a condensed phase in the work-up section of the plant in which the content of isocyanate or phosgene is below 5% by volume, preferably below 3% by volume, particularly preferably below 1% by volume,
(b) measurement of at least one signal which is generated by the at least one measurement probe and
(c) measurement of entry of water into the plants by monitoring the at least one signal.

The method of the invention thus makes it possible to monitor plants for preparing isocyanates successfully and makes it possible to react immediately to entry of water before greater corrosion damage occurs on the plants.

The method serves, in particular, to monitor plants in which water-free process streams are present and in which the corrosivity of the process streams increases greatly on intrusion of water, even in extremely small amounts, for example in the region of about 100 ppm, due to the formation of aqueous hydrochloric acids. Such plants are plants for preparing isocyanates, acid chlorides, polycarbonates and acid anhydrides. In the case of isocyanates, the plants are preferably those in which at least one isocyanate from the group consisting of methylenedi(phenyl isocyanate) (MDI), tolylene diisocyanate (TDI), hexamethylene diisocyanate, pentamethylene diisocyanate (HDI), isophorone diisocyanate (IPDI), 2,4- and 2,6-diisocyanatomethylcyclohexane is prepared.

According to the invention, one or more measurement probe(s) are introduced in step (a) into a condensed phase in the work-up section of the plants in which the content of isocyanate or phosgene is below 5% by volume, preferably below 3% by volume, particularly preferably below 1% by volume. The introduction or arrangement of the measurement probe(s) in the work-up section of the plants in a condensed phase in which the content of isocyanate or phosgene is below 5% by volume, preferably below 3% by volume, particularly preferably below 1% by volume, makes it possible to detect traces of water which can, for example, enter via leaks at sealing elements, welding seams or corrosion points into the plants by measuring the at least one signal which is generated by the at least one measurement probe in step (b) and monitoring the signal in step (c) and recognize corrosive states preventively and at an early stage. This considerably increases the availability of the plants since fewer corrosion-related downtimes occur. In the context of the invention, it has been found that, particularly in the work-up section of these plants, the occurrence of corrosion can in this way be observed in good time. This is probably related to the fact that good mixing and high temperatures prevail in the reaction section of the plants, which favors and accelerates the reaction of isocyanate with water which enters, as a result of which virtually no corrosion can occur in this region of the plants.

The arrangement of measurement probes at endangered places such as heat exchangers, as disclosed in DD 139 955, makes it possible to detect drastic intrusion of water, but the use of these probes is restricted exclusively to phosgene-conducting plant components.

The introduction of at least one measurement probe into a condensed phase in the work-up section of the plants which has a low content of phosgene and in which the isocyanate content is below 5% by volume, preferably below 3% by volume, particularly preferably below 1% by volume, means, in the context of the invention, that the measurement probe can preferably be installed at places such as pipes which serve to transport liquid streams, reservoirs for operating medium of vacuum pumps, at pipes at the top of columns, in particular at the top of vacuum columns or at places such as condensers at the top of distillation or rectification columns which are operated under reduced pressure. Particular preference is given to installation of the measurement probes at the top of columns, preferably at the top of vacuum columns, or the pipes downstream of vacuum columns or the vacuum columns themselves, in particular when the vacuum plant is configured as a liquid ring compressor.

For the purposes of the invention, "plants for preparing isocyanates by reacting phosgene with one or more primary amine(s) in a solvent" are plants in which the phosgenation of the amine or the amines is carried out using phosgene in the presence of a solvent or solvent mixture in a liquid phase. In a further embodiment of the invention, "plants for preparing isocyanates by reacting phosgene with one or more primary amine(s) in a solvent" are plants in which the isocyanates are prepared by reaction of phosgene and amine in the gas phase and are subsequently, for example in a quench, dissolved in a solvent.

As solvents, it is possible to use solvents which are generally suitable for the preparation of isocyanates. These are preferably inert aromatic, aliphatic or cyclic hydrocarbons or halogenated derivatives thereof. Examples of such solvents are aromatic compounds such as monochlorobenzene or dichlorobenzene, for example o-dichlorobenzene, toluene, xylenes, naphthalene derivatives such as tetralin or decalin, alkanes having from about 5 to about 12 carbon atoms, e.g. hexane, heptane, octane, nonane or decane, cycloalkanes such as cyclohexane, largely inert esters and ethers, e.g. ethyl acetate or butyl acetate, tetrahydrofuran, dioxane or diphenyl ether. In a preferred embodiment, the solvent is selected from the group consisting of monochlorobenzene, dichlorobenzene, cyclohexane and toluene.

Suitable amines are in principle all primary amines which can react in a suitable way with phosgene to form isocyanates. All linear or branched, saturated or unsaturated aliphatic or cycloaliphatic or aromatic primary monoamines or polyamines which can be reacted with phosgene to form isocyanates are suitable. Examples of suitable amines are 1,3-propylenediamine, 1,4-butylenediamine, 1,5-pentamethylenediamine, 1,6-hexa-methylenediamine and the corresponding higher homologues of this series, isophoronediamine (IPDA), cyclohexylenediamine, cyclohexylamine, aniline, phenylenediamine, p-toluidine, 1,5-naphthylenediamine, 2,4- or 2,6-tolylenediamine or mixtures thereof, 4,4'-, 2,4'- or 2,2'-diphenylmethanediamine or mixtures thereof and also higher molecular weight isomeric, oligomeric or polymeric derivatives of the abovementioned amines and polyamines.

The reaction of phosgene with amines occurs in a reaction space in the reaction section of the plants, which is generally arranged in a reactor, i.e. the reaction space is the space in which a part of the reaction of the starting materials and/or intermediates which is relevant to the yield of the process occurs and the isocyanate is thus formed. The reactor is the technical apparatus comprising the reaction space. All customary reaction spaces known from the prior art which are suitable for preparing isocyanates are possible here.

In an embodiment of the invention, the reaction section is preceded by a mixing device in which the starting materials, viz. the phosgene and the at least one primary amine, and also the solvent, which may also be fed to the reaction in the form of a mixture with phosgene and/or amine, are mixed and subsequently fed to the reaction section. The mixing unit can be, for example, a mixing nozzle.

After the starting materials have been reacted in the reaction section of the plants, the reaction mixture obtained is conveyed to the work-up section of the plant.

For the purposes of the present invention, the term "work-up section" refers to the section of the plants in which one or more column-like systems are arranged for the thermal separation of isocyanate, solvent and, if appropriate, by-product. The reaction mixture, which consists essentially of the isocyanates, the solvent, hydrochloric acid and phosgene, is separated into its constituents in this section of the respective plant by means of distillation and/or rectification and also, if appropriate, thermal residue treatment in kneaders or paddle dryers, with the solvent being able to be returned to the reaction section of the plant. In the context of the invention, it has been observed that the occurrence of corrosive medium conditions in the plants can be detected particularly well and the occurrence of corrosion can thus be effectively prevented by the introduction or arrangement of measurement probes in the work-up section of the plant.

For the purposes of the invention, the term "measurement probe" refers to electrodes or sensors or components which can provide a signal which is a measure of corrosion. Such measurement probes are known to those skilled in the art, for example from DE-A 28 09 322 and DD-A 139 955. In an embodiment of the invention, it has been found to be advantageous to introduce a measurement probe which comprises a resistance wire and, in particular, is based on the principle of electrical resistance measurement in step (a).

The resistance wire comprises materials which have a lower corrosion resistance than the materials of the apparatuses and pipes of the plant but during proper operation of the plant have a corrosion resistance which is sufficiently high for the function of the probe to be ensured over a number of months. Materials suitable for this purpose are metals from the group consisting of Zn and Fe and also low-alloy or high-alloy steels and also nickel-based alloys known to those skilled in the art.

In the event of entry of water, aqueous hydrochloric acid is formed in the plants in the presence of low HCl concentrations. The more corrosive medium conditions which result preferentially attack the less corrosion-resistant wire of the probe and to a lesser extent the apparatuses and pipes of the plant itself, which leads to a reduction in the cross section of the wire and thus to a decrease in the flow of current and an increase in the electrical resistance. This increase is measured by methods known to those skilled in the art, for example by means of a Wheatstone bridge. During operation of the apparatus, the signal or signals provided by the measurement probes is/are permanently measured and monitored in step (b) in order to be able to detect possible entry of water into the apparatus. If the change in the signal points to intrusion of water, the plant can be immediately shut down or repaired before damage due to corrosion occurs.

Figure 2:
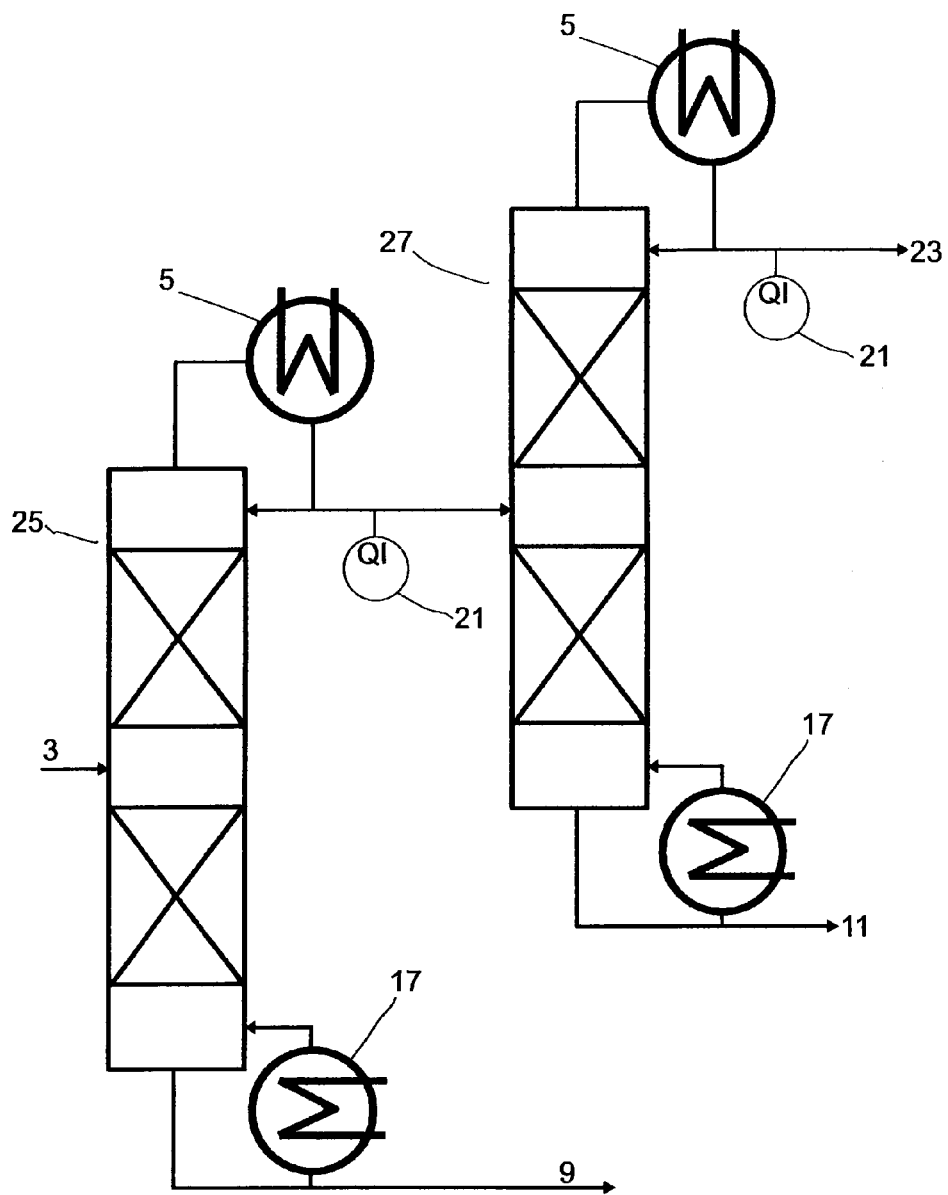

The invention is illustrated by the following examples:

Preferred embodiments of the method of the invention are shown schematically in FIGS. 1 and 2.

EXAMPLE 1

FIG. 1 shows, by way of example, the separation of an isocyanate stream 3 from high boilers 19 with simultaneous isolation of the pure isocyanate 9. The distillation column 1 with vaporizer 17 which is used for this purpose is operated under reduced pressure. While the isocyanate 9 is condensed in the condenser 5, the low-boiling components such as HCl, phosgene or secondary components occurring in the synthesis and the leakage air go to the vacuum pump 7. A liquid ring pump 7 is used for generating the vacuum. The solvent used in the isocyanate process, for example monochlorobenzene or toluene, is used as operating medium 11 for the liquid ring pump 7.

Traces of hydrogen chloride liberated in the distillation are partly absorbed by the operating medium 11 of the vacuum pump 7 from the exhaust air stream 15 and accumulate in stream 13. The water which gets into the system in the form of moisture as a result of usual technical leakage rates and leakage air is likewise absorbed and accumulates. The targeted positioning according to the invention of the measurement probe 21 in the work-up section of the plant, in this case in stream 13, enables the entry of water to be monitored in a targeted manner.

The concentration of hydrogen chloride and water established depend, during operation of the plant, on the solvent stream introduced and discharged and in normal operation are too low to cause corrosion. During operation of the plant, the measurement probe 21 shows a value which does fluctuate but overall remains at a constant level and is characteristic of the installation position.

If entry of water into the system occurs, for example due to leaks in heat exchangers operated using steam or cooling water or increased leakage rates in the vacuum pumps 7, the water content increases and together with the hydrogen chloride present results in an increase in the corrosivity of the operating medium. The value measured by the measurement probe 21 installed increases correspondingly.

The measurement of the increased corrosion rate is so sensitive that there is sufficient time for a search for defects or countermeasures.

EXAMPLE 2

FIG. 2 shows, by way of example, a section of the work-up by distillation of product streams 3 in the work-up section of isocyanate plants.

In the first distillation column 25 with heat exchanger 17 and condenser 5, the solvent 11, for example monochlorobenzene or toluene, is separated off at the top. The solvent 11 obtained in this way still comprises traces of other low-boiling substances occurring in the process, e.g. HCl, phosgene or secondary components occurring in the synthesis. This solvent 11 cannot be reused in the process without further treatment. In a second distillation column 27, heat exchanger 17 and condenser 5, the solvent 11 is purified by the low boilers 23 with a certain proportion of the solvent 11 being separated off at the top and treated further at another place in the process.

In normal operation, the measurement probes 21 indicate a very low constant measured value.

If water gets into the system due to a malfunction, for example leakage in a heat exchanger of the first distillation column 17 operated by means of steam or water, the water will get into the solvent 11 at the top of the column 25. Together with the hydrogen chloride, HCl, which is likewise present there, a corrosive solvent mixture is formed. This is recognized by the measurement probe 21 and leads to an increase in the signal.

Furthermore, the corrosive solvent mixture goes into the second distillation column 27. The water and hydrogen chloride which have lower boiling points than the solvent 11 are separated off at the top and once again form a correspondingly corrosive condensate. This is recognized with a time delay by the measurement probe 21 which is arranged at the tope of the second distillation column.

When measurement probes covering the entire process are used, the point of entry of the water can thus be localized and extent of spread in the process can be understood.

The invention claimed is:

1. A method of measuring entry of water into an isocyanate preparation plant comprising a reaction section and a work-up section, the method comprising:
   (a) introducing a measurement probe into a condensed phase in the work-up section in which a content of isocyanate or phosgene is below 5% by volume,
   (b) measuring a signal genereated by the measurement probe and
   (c) monitoring the signal, thereby measuring entry of water into the plant.

2. The method of claim 1, wherein the measurement probe comprises a resistance wire.

3. The method of claim 1, wherein the signal is a flow of current through the measurement probe.

4. The method of claim 1, further comprising:
   separating a solvent from a product isocyanate in the work-up section of the plant and
   recirculating the solvent to the reaction section.

5. The method of claim 1, further comprising:
   separating a solvent from a product isocyanate in the work-up section of the plant in a column system.

6. The method of claim 1, further comprising:
   separating a solvent from a product isocyanate by distillation, rectification, extraction, or a combination thereof.

7. The method of claim 1, wherein introducing the measurement probe comprises introducing the measurement probe at a vacuum pump with a solvent as an operating medium.

8. The method of claim 1, further comprising preparing at least one isocyanate selected from the group consisting of methylenedi(phenyl isocyanate), tolylene diisocyanate, hexamethylene diisocyanate, pentamethylene diisocyanate, isophorone diisocyanate, 2,4-diisocyanatomethylcyclohexane, and 2,6-diisocyanatomethylcyclohexane.

9. The method of claim 1, further comprising preparing an isocyanate in a reaction in at least one solvent selected from the group consisting of monochlorobenzene, dichlorobenzene, cyclohexane, and toluene.

10. The method of claim 7, further comprising preparing isocyanate in a solvent that is the vacuum pump operating medium solvent.

11. A method for preparing an isocyanate, comprising:
   reacting phosgene with a primary amine in a solvent, in a plant comprising a reaction section and a work-up section, and
   measuring entry of water into the plant by the method of claim 1.

12. The method of claim 11, wherein the isocyanate is at least one isocyanate selected from the group consisting of methylenedi(phenyl isocyanate), tolylene diisocyanate, hexamethylene diisocyanate, pentamethylene diisocyanate, isophorone diisocyanate, 2,4-diisocyanatomethylcyclohexane, and 2,6-diisocyanatomethylcyclohexane.

13. The method of claim 11, wherein the solvent is at least one solvent selected from the group consisting of monochlorobenzene, dichlorobenzene, cyclohexane, and toluene.

14. The method of claim 11, wherein a content of isocyanate or phosgene in the work-up section is below 5% by volume.

15. The method of claim 11, wherein a content of isocyanate or phosgene in the work-up section is below 3% by volume.

16. The method of claim 11, wherein a content of isocyanate or phosgene in the work-up section is below 1% by volume.

* * * * *